United States Patent [19]

Bennett

[11] 4,210,156
[45] Jul. 1, 1980

[54] FINGER STICK BLOOD COLLECTION APPARATUS

[76] Inventor: Elmer T. Bennett, 2018 Dickinson St., Philadelphia, Pa. 19046

[21] Appl. No.: 899,150

[22] Filed: Apr. 24, 1978

[51] Int. Cl.² .............................................. A61B 5/14
[52] U.S. Cl. ..................... 128/763; 128/766; 128/276; 73/425.4 P
[58] Field of Search ............... 206/820; 222/420, 421; 215/306, 250, 253, 346; 128/233, 275, 2 F, 231, 232, 760, 763; 141/8, 72; 73/425.4 P, 425.6; D9/10, 261, 262; 422/100, 102

[56] References Cited

U.S. PATENT DOCUMENTS

| 2,423,173 | 7/1947 | Brady et al. ........................ 422/100 |
| 2,664,752 | 1/1954 | Southwick ........................... 422/100 |
| 2,707,469 | 5/1955 | Feinstein .............................. 128/233 |
| 3,088,617 | 5/1963 | Krautkramer ...................... 215/250 |
| 3,141,336 | 7/1964 | Oates ................................... 422/100 |
| 3,881,527 | 5/1975 | Shapiro ............................... 222/420 |

Primary Examiner—Robert W. Michell
Assistant Examiner—J. L. Kruter
Attorney, Agent, or Firm—Seidel, Gonda, Goldhammer & Panitch

[57] ABSTRACT

Apparatus for collection of a blood sample from a finger stick includes a collection vessel removably connected to a cap. The cap has a passage therethrough between a hollow adaptor connected to the cap and extending in an opposite direction from the vessel. The adaptor facilitates introducing blood into the vessel by creating a vacuum in the vessel and adaptor. For shipment of the blood sample, the open ends of the adaptor and vessel are closed by means of a plug and then the cap is removably secured to the open end of a container into which the vessel extends.

9 Claims, 3 Drawing Figures

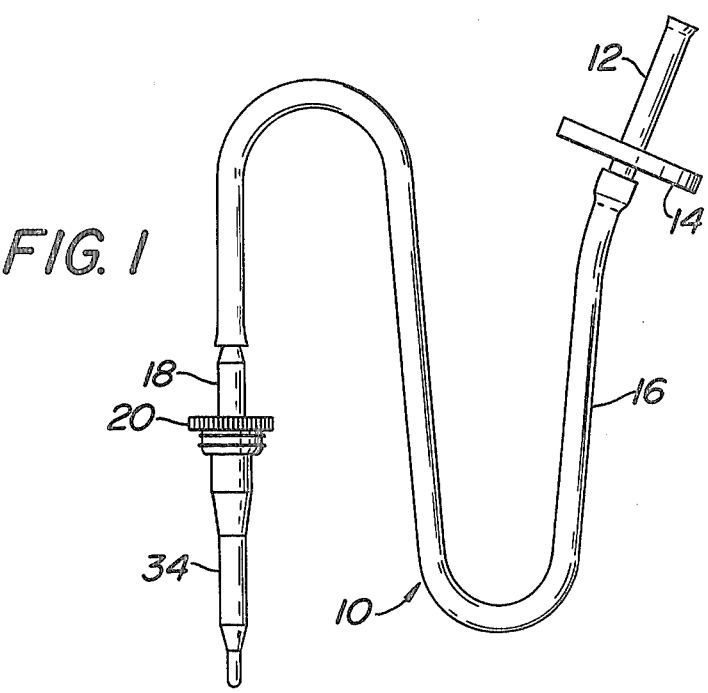

FINGER STICK BLOOD COLLECTION APPARATUS

BACKGROUND

Instead of taking blood by way of a needle from a vein, a small sample of blood can be obtained by means of a finger stick. A finger stick describes the process of puncturing the skin with a small sharp blade and obtaining a small sample of blood which enters a small vessel by way of capilliary action. In order to fill a small vessel, generally having a capacity less than 1 milliliter, by way of capilliary action, it is necessary to maintain a small pool of blood on the finger. Obtaining a blood sample by way of a finger stick in a capilliary vessel has many disadvantages. For example, the small pool of blood frequently runs thereby interrupting the capilliary action. The entry of a bubble into the capilliary tube creates problems and prevents obtaining a sufficient blood sample. Also, it is necessary to massage a finger in order to obtain a sufficient sample depending upon where the stick occurred. All of these disadvantages are solved by the present invention.

SUMMARY OF THE INVENTION

The present invention is directed to apparatus for collection of a blood sample from a finger stick. The apparatus includes a collection vessel which preferably has a capacity of 1 to 2 milliliters. The collection vessel has a first end having transverse dimensions greater than the transverse dimensions at its second end. The first and second ends of the vessel are open.

The apparatus includes a cap having transverse dimensions greater than the transverse dimensions of said first end of said vessel. A means is provided for releasably coupling said first end of said vessel to said cap. A hollow adaptor is connected to said cap and is preferably integral therewith in one piece. The adaptor is hollow and communicates with the interior of the vessel by way of a passage in the cap. The free end of the hollow adaptor is open and is provided with means adapted to facilitate connection of the adaptor to a source of vacuum.

The apparatus includes a shipping container open at one end and of sufficient dimensions to receive the vessel therein. A means is provided on the cap radially outwardly from the first end of the vessel for releasably coupling said cap to said open end of the container. A separate means is provided to temporarily close the free end of the adaptor and the second end of the vessel during shipment of the vessel in said container.

It is an object of the present invention to provide apparatus for collection of a small blood sample from a finger stick by causing blood in the microliter range up to 2 milliliters to be sucked into the vessel.

It is another object of the present invention to provide apparatus for collection of small amounts of blood from a finger stick by sucking the blood into a vessel so that entry of air bubbles has no effect on attaining a sufficient sample.

Other objects will appear hereinafter.

For the purpose of illustrating the invention, there is shown in the drawings a form which is presently preferred; it being understood, however, that the invention is not limited to the precise arrangements and instrumentalities shown.

FIG. 1 is a plan view of apparatus in accordance with the present invention.

FIG. 2 is an enlarged sectional view of portions of the apparatus.

FIG. 3 is a sectional view of portions of the apparatus in a shipping container.

Referring to the drawings in detail, wherein like numerals indicate like elements, there is shown apparatus in accordance with the present invention designated generally as 10. The apparatus 10 includes a mouthpiece 12 connected by way of a filter 14 to one end of a flexible tube 16. The flexible tube 16 is connected at its other end to an adaptor 18. Elements 12–16 constitute a means for creating a vacuum in adaptor 18 by inhaling on the mouthpiece 12.

The adaptor 18 is integral in one piece with a cap 20. Adaptor 18 has a free end and is smooth or barbed in any convenient manner so as to facilitate coupling the free end to the tube 16. The cap 20 has a flow passage 22 providing communication with the interior 24 of the adaptor 18.

When the cap 20 is injection molded from a polymeric plastic, the adaptor 18 is integral therewith as well as plugs or closures 26, 28. The plugs or closures 26, 28 extend in opposite directions from the cap and are integral therewith by means of a narrow weak web which is easily broken for a purpose to be made clear hereinafter.

In a direction extending opposite from the direction of adaptor 18, the cap 20 is provided with concentric annular flanges 30, 32. Flange 32 is longer than flange 30. In the annular cavity between the flanges 30, 32, a collection vessel 34 is removably coupled to the cap 20. Such removable coupling may be a force-fit, a snap-fit, or threads. Vessel 34 may be molded or otherwise formed from a transparent polymeric plastic or glass and preferably has a capacity of 1 to 2 milliliters. In a typical one milliter embodiment, the vessel 34 has a length of 42 millimeters and tapers from a large diameter end 35 to a small diameter end. The inner transverse dimensions of the vessel 34 expand rapidly at portion 35 which is tapered at an angle of about 15 degrees with respect to the vertical as shown in FIG. 2 whereby air bubbles sucked into vessel 34 are induced to separate. The vessel large diameter end 35 removably coupled to the cap 20 may have a diameter of approximately 7 millimeters while the small diameter end 37 has a outer diameter of 2 millimeters with the entry port at the small diameter end being between 0.5 and 1.0 millimeters. The adaptor 18 is shorter than the length of the vessel 34.

A shipping container 36 is provided. Container 36 is open at one end. The open end of the container 36 is adapted to be removably coupled to the cap 20 in any convenient manner such as being force-fit over flange 32, a snap-fit over flange 32, or by means of screw threads. The outer diameter of cap 20, excluding the plugs or closures 26 and 28, corresponds generally to the outer diameter of container 36. The outer periphery of cap 20 may be provided with knurling or milling to facilitate the ease of turning cap 20 relative to the container 36.

The apparatus of the present invention is utilized as follows. A container 36 is removably coupled to a cap 20. The plugs or closures 26 and 28 are snapped off and placed to one side. Adaptor 18 is connected to one end of the tube 16. The apparatus is now in condition for collecting a blood sample.

By means of a blood stick, blood is caused to appear on a finger or other portion of a person at any place wherein the incision is made. The operator has the mouthpiece 12 in his mouth and inhales thereby evacuating vessel 30 and adaptor 18. The small diameter end of the vessel is placed in contact with the blood which immediately enters the vessel 34. Due to the volume and capacity of the vessel 34, any air bubbles which enter automatically separate and pass upwardly through the adaptor 18 into the tube 16 whereby blood entry into the vessel is not interrupted by such air bubbles. The operator may observe the amount of blood introduced into the vessel 34 due to the transparency of vessel 34. As soon as a sufficient sample is observed in the vessel 34, the operator takes one of the plugs or closures 26 and 28 and closes the small open end of the vessel 34 while terminating any inhalation causing a vacuum in tube 16.

Thereafter, adaptor 18 is uncoupled from the tube 16. The remaining one of the plugs or closures 26 and 28 is snapped over the open end of adaptor 18. Thereafter, the thusly described assembly is introduced into the container 36 and shipped to a laboratory. At a laboratory, the cap 28 and container 26 are separated. Thereafter, the vessel 34 is separated from the cap 20 and the sample is analyzed. Each of the adaptor 18, cap 20, vessel 34, and container 36 may be discarded after a single use. If desired, the cap 20 with its adaptor and the container 36 may be reused after removing any identifying indicia on the container 36 relating to a particular previous patient from whom blood was taken.

The vessel 36 is preferably made from any one of a wide variety of rigid transparent materials such as glass or a polymeric plastic material capable of being sterilized. If desired, the interior surface of vessel 34 may be coated with an anti-coagulant or some other material depending upon the type of blood test being performed.

Other devices may be utilized to create the partial vacuum in the vessel 34 but such devices are preferably of the type which do not require the operator to use one hand to manipulate the same. As will be apparent from the above description, with the mouthpiece 12 in a person's mouth, the operator has one hand free and one hand for manipulating the vessel 34. This is preferred over any type of vacuum creating device which requires the operator to use both hands whereby the operator does not have one hand free to steady the patient. The rate of entry of blood into the vessel 34 may be amplified by applying a tourniquet on the patient's arm above the point where the blood stick is made.

The present invention may be embodied in other specific forms without departing from the spirit or essential attributes thereof and, accordingly, reference should be made to the appended claims, rather than to the foregoing specification as indicating the scope of the invention.

I claim:

1. Finger stick blood collection apparatus comprising a collection vessel for collecting blood from a finger stick and having a capacity of less than two milliliters, said vessel having first and second open ends, said first end of said vessel having larger transverse dimensions than said second end, the smallest transverse dimension of said vessel being at said second end, said vessel having a portion adjacent said second end which is tapered toward said second end, said second end being the inlet end to said vessel, a cap having transverse dimensions greater than that of said first vessel end, means releasably coupling said first end of said vessel to one side of said cap, a hollow adapter connected at one end to and integral with the other side of said cap, the other end of said adapter being free and having means for a facilitating connection of the adapter to a source of suction, said cap having a flow passage therethrough for providing direct communication with the interior of said adapter and the interior of said vessel, separate means for temporarily closing said collection vessel, said vessel being expendable after a single use, a shipping container for said vessel, said container being open at one end, said vessel with its second end temporarily closed being disposed within said container, means on said cap radially outwardly of said first end of said vessel releasably coupling said cap to close said container.

2. Apparatus in accordance with claim 1 wherein said adaptor is shorter than the length of said vessel, the free end of said adaptor and said second end of said vessel each having a flow port of about 0.5 to 1.0 millimeters in diameter.

3. Apparatus in accordance with claim 1 wherein one end of a flexible tube is coupled to the free end of said adaptor, the other end of said flexible tube being connected to a mouthpiece to facilitate creating a vacuum in said vessel.

4. Apparatus in accordance with claim 1 wherein said vessel is an transparent vessel having transverse dimensions which decrease progressively from said first end to said second end.

5. Apparatus in accordance with claim 1 wherein the transverse dimensions of said first end of said vessel and the transverse dimensions of said adapter adjacent said cap being greater than the transverse dimensions of said flow passage through said cap.

6. Apparatus for collection of a blood sample from a finger stick comprising a collection vessel having a capacity of not more than 2 milliliters, said vessel being open at both ends, a first end of said vessel having larger transverse dimensions that said second end, said vessel being transparent, a cap having transverse dimensions greater than the transverse dimensions of said vessel first end, means for releasably coupling said first end of said vessel to one side of said cap to a hollow adaptor being in one piece at one end thereof with the other side of said cap, said adaptor being shorter than said vessel and extending from said cap in a direction away from said vessel while being generally coaxial with said vessel, said cap having a flow passage providing communication between the interior of said adaptor and the interior of said vessel, the other end of said adaptor being open and provided with means to facilitate coupling the adaptor to a source of vacuum, a first closure adapted to be applied to said other end of said adaptor for temporarily closing said other end of said adaptor, a second closure adapted to be applied to said second end of said vessel for temporarily closing the same.

7. Apparatus in accordance with claim 6 including a shipping container open at one end, said shipping container having means on its open end for cooperating with said cap outer periphery to removably couple said cap and container, said vessel being disposed entirely within said container.

8. Apparatus in accordance with claim 6 including a mouthpiece coupled to said adaptor by way of a flexible tube to facilitate creating a vacuum in said vessel.

9. Apparatus in accordance with claim 6 wherein the flow passage at said second end of said vessel and the flow port at said other end of said adaptor is about 0.5 to 1.0 millimeters in diameter.

* * * * *